US008602962B2

(12) United States Patent
Gavish et al.

(10) Patent No.: US 8,602,962 B2
(45) Date of Patent: Dec. 10, 2013

(54) ACUPRESSURE MAGNETIC THERAPY GLOVE

(76) Inventors: Shlomi Gavish, Hollywood, FL (US); Gady Abramson, Hollywood, FL (US)

( * ) Notice: Subject to any disclaimer, the term of this patent is extended or adjusted under 35 U.S.C. 154(b) by 267 days.

(21) Appl. No.: 13/007,055

(22) Filed: Jan. 14, 2011

(65) Prior Publication Data

US 2011/0178360 A1  Jul. 21, 2011

Related U.S. Application Data

(60) Provisional application No. 61/295,204, filed on Jan. 15, 2010.

(51) Int. Cl.
*A61N 1/00* (2006.01)
(52) U.S. Cl.
USPC ............................... 600/15; 606/204; 2/161.7
(58) Field of Classification Search
USPC ................. 600/9, 13–15; 606/201, 204; 2/159–160, 161.7; 128/24; 601/134–137
See application file for complete search history.

(56) References Cited

U.S. PATENT DOCUMENTS

| 5,405,310 | A | 4/1995 | Yoo |
| 5,405,357 | A | 4/1995 | Rowe-Lanzisera |
| 5,720,046 | A * | 2/1998 | Lopez et al. ............. 2/159 |
| 6,986,779 | B2 * | 1/2006 | Begley et al. ............ 606/204 |
| 2005/0101828 | A1 | 5/2005 | Butler |
| 2006/0190026 | A1 * | 8/2006 | Sanders ............. 606/204 |

* cited by examiner

*Primary Examiner* — Christine Matthews
*Assistant Examiner* — Laura Fajardo
(74) *Attorney, Agent, or Firm* — Mark D. Bowen; Malin Haley DiMaggio & Bowen, P.A.

(57) ABSTRACT

A therapeutic glove specifically adapted to simultaneously apply a combination of acupressure and magnetic therapy to specific acupoint sites on the hand resulting in therapeutic benefits, including providing an effective headache remedy is disclosed. A fingerless glove incorporates an inflatable bladder disposed formed on the palm of the glove for application of acupressure to HT-8 and PC-8 acupoints. A hand-pump is in pneumatic communication with the bladder and functions to allow the user to inflate the bladder to a desired pressure. First and second permanent magnets are disposed on the dorsal portion of the glove and disposed so as to be in covering relation with the TH-3 and LI-4 acupoints. An adjustable dorsal strap is configured to wrap over the first and second permanent magnets as well as the bladder thereby providing a compressive force. Inflation of the bladder results in compression that functions to maximize the benefits of magnetic therapy by biasing the magnets towards the acupressure points from the dorsal side of the hand while providing the ability to control the air pressure using a hand pump.

4 Claims, 6 Drawing Sheets

ACUPRESSURE MAGNETIC THERAPY GLOVE

CROSS REFERENCE TO RELATED APPLICATIONS

This application claims the benefit of provisional U.S. patent application Ser. No. 61/295,204, filed on Jan. 15, 2010.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights rights whatsoever.

BACKGROUND OF THE INVENTION

1. Field of the Invention

The present invention relates generally to a glove apparatus for use in connection with a combination of acupressure treatment and magnetic therapy to alleviate pain associated with headaches and migraines, and to improve blood flow throughout the body to relieve neck, shoulder, and elbow pain, carpal tunnel syndrome and premenstrual symptoms.

2. Description of Related Art

Acupressure, a treatment widely accepted by the medical community and the public, is a non-invasive form of acupuncture. Acupuncture points, or acupoints, are locations on the body that are the focus of acupuncture, acupressure, and other treatment methodologies. Several hundred acupuncture points are considered to be located along meridians, which comprise connected points across the anatomy which affect a specific organ or other part of the body. Certain acupuncture points are ascribed different functions according to different systems within the frame work of Traditional Chinese Medicine (TCM) theory.

For example, the Large Intestine (LI) Meridian generally includes 20 acupuncture points running from LI-1 located posterior to the corner of the nail on the radial side of the index finger, to LI-20 located in the nasolabial groove, level with the midpoint of the lateral border of the ala nasi. The LI-4 Acupuncture Point-He Gu-Large Intestine Meridian is located in the middle of the $2^{nd}$ metacarpal bone on the radial side of the hand, and is associated with headaches (especially frontal and or sinus (yangming area), chronic pain, problems on the face, and the circulation of blood, among other issues.

The Triple Heater (TH) Meridian generally includes 23 acupuncture points running from TH-1 located posterior to the corner of the nail on the ulnar side of the ring finger, to TH-23 located in a depression at the lateral end of the eyebrow. The TH-3 Acupuncture Point-Zhong Zhu-Triple Heater Meridian is located on the dorsum of the hand between the $4^{th}$ and $5^{th}$ metacarpal bones in a depression proximal to the $4^{th}$ metacarpalphalangeal joint, and is associated with ear problems of any etiology such as tinnitus, and as a distal point for temporal headaches, shoulder and/or upper back pain.

The Heart Meridian (HT) generally includes 9 acupuncture points running from HT-1 located in the center of the axilla on the radial side of the axillary artery to HT-9 located on the radial side of the little finger. The HT-8 Acupuncture Point-Shao Fu-Heart Meridian is located where the tip of the little finger rests between the $4^{th}$ and $5^{th}$ metacarpal bones when making a fist, and is associated with heart deficiencies and emotional disorders.

The Pericardium Meridian (PC) generally includes 9 acupuncture points running from PC-1 located 1 can lateral to the nipple in the $4^{th}$ ICS, to PC-9 located in the center of the tip of the middle finger. The PC-8 Acupuncture Point-Lao Gong-Pericardium Meridian is located at the center of the palm between the $2^{nd}$ and $3^{rd}$ metacarpal bones closer to the radial side of the $3^{rd}$, where the tip of the middle finger falls when a loose fist is made, and is associated with excess heat conditions, heat in the mouth, mouth or tongue ulcers, cold sores, cooling the blood, blood in the stool or urine, and nosebleeds.

Acupressure is a blend of "acupuncture" and "pressure" involving the application of physical pressure upon identified points on the body, namely specific acupuncture points or acupoints. The pressure is intended to transfer energy throughout the body to stimulate blood flow such that pain and/or discomfort is reduced or alleviated.

Magnetic therapy is an alternative medicine practice involving the use of static magnetic fields by application of permanent static magnets to the body for health benefits. Some practitioners assign different effects based on the position and orientation of the magnet relative to the body. A number of products have been developed to realize the benefits of magnetic therapy, including magnetic bracelets and jewelry, magnetic straps for the wrists, ankles, knees, and back, show inserts, matresses, and blankets.

The background art reveals a number of devices intended to harness the beneficial effects of acupressure and magnetic therapy. For example, U.S. Pat. No. 5,405,310, issued to Yoo, discloses an acupressure glove adapted with a plurality of acupressure protuberances for applying acupressure to the hand. The device disclosed by Yoo, however, is limited to a non-adjustable glove that does not allow for any adjustment of the pressure applied. Similarly, U.S. Pat. No. 5,405,357, issued to Rowe-Lanzisera et al., discloses an acupressure glove device for providing self-stimulation of acupressure points on the hand and wrist. Rowe-Lanzisera et al., however, require that the user apply direct pressure to locators on the exterior surface of the glove whereby the pressure is applied through the glove to underlying nodules. Published U.S. Application No. 2006/0190026, in the name of Sanders discloses an adjustable acupressure device intended to apply pressure to a specific portion of the user's body when disposed in an operative position. The device includes an attachment assembly having at least one placement indicator for facilitating accurate placement of the device, and a pressure assembly, including a pressure applicator structured to contact a specific point on the user's body, and further allowing the user to apply a desired amount of pressure to the specific portion of the user's body.

The present inventor has found that the application of acupressure in combination with magnetic therapy to specific acupoints identified above (HT-8, PC-8, TH-3, and LI-4) achieves unexpected therapeutic results and benefits. More particularly, the present inventor has found that the combination of acupressure and magnetic therapy when applied to the HT-8, PC-8, TH-3, and LI-4 acupoints provides relief of headaches among other benefits. While the devices reveled in the background art appear generally suitable for the specific applications and uses for which they are intended, they fail to maximize therapeutic effects by combining the benefits of acupressure and magnetic therapy. The devices of the background art further fail to provide a therapeutic glove apparatus that simultaneously applies acupressure to the four specific acupoints, HT-8 and PC-8 (on the palm of the hand), and TH-3 and LI-3 (on the back of the hand) in combination with the application of magnetic therapy.

BRIEF SUMMARY OF THE INVENTION

The present invention overcomes the limitations present in the art by providing a therapeutic glove specifically adapted to simultaneously apply a combination of acupressure and magnetic therapy to specific acupoint sites on the hand resulting in unexpected therapeutic benefits, including providing an effective headache remedy. An acupressure glove in accordance with the present invention preferably comprises a fingerless glove that incorporates an inflatable bladder removably received within a pocket formed on the palm of the glove for application of acupressure to HT-8 and PC-8 acupoints. A hand-pump is in pneumatic communication with the bladder and functions to allow the user to inflate the bladder to a desired pressure. The glove further includes first and second permanent magnets located on the dorsal portion of the glove and disposed so as to be in covering relation with the TH-3 and LI-4 acupoints. An adjustable wrist strap is configured for being secured around the user's wrist to aid in securing the glove to the user's hand, and an adjustable dorsal strap is configured to wrap over the first and second permanent magnets thereby providing a compressive force. Inflation of the bladder results in compression that functions to maximize the benefits of magnetic therapy by biasing the magnets towards the acupressure points from the dorsal side of the hand while providing the ability to control the air pressure using a hand pump.

A glove in accordance with the present invention functions to stimulate blood flow to specific areas of the body by applying pressure to four different points on the hand, and has been found to be particularly effective in reliving headaches. The first pressure point is identified as LI-4, found between the index finger and thumb on the dorsal side of the hand. Application of pressure to this point alleviates frontal headache or sinus pain, improves immunity, and treats problems on the face including: mouth, teeth, jaw, allergies, rhinitis, acne, and eye problems. The second pressure point is identified as TH-3, found between the fourth and fifth metacarpal bones in a depression proximal to the fourth metacarpalphalangeal joint on the dorsal side of the hand. Application of pressure to this point alleviates temporal headaches, shoulder, upper back pain, and ear problems such as tinnitus. The third pressure point is identified as HT-8, found between the fourth and fifth metacarpal bones on the palm side of the hand. Application of pressure to this point relieves bio-social and psychological stress to relieve headaches associated therewith. The fourth pressure point is identified as PC-8, found between the second and third metacarpal bones on the palm side of the hand. Application of pressure to this point relieves excess heat in the body, mouth or tongue ulcers, nosebleeds, and blood in the stool or urine.

As noted above, the glove is adapted with first and second magnets located over the LI-4 and TH-3 pressure points on the dorsal side of the hand, and an inflatable bladder disposed on the palm side. A strap is first secured about the glove so that the apparatus fits the hand snuggly and encircles the bladder and magnets to provide a compressive band. The bladder is then filled with air by using the attached hand pump until pressure is felt by the wearer. The amount of pressure required is individualized, depending upon the severity of the headache, or pain. The greater the pressure applied, the greater the energy flow throughout the body. The treatment is intended to work within ten to twenty minutes, and may be used several times a day, or as needed. The glove is comfortable and transportable, and utilizes magnets on the indicated pressure points and air pressure from the bladder to achieve beneficial results by combining the therapeutic effects of acupressure and magnetic therapy.

Accordingly, it is an object of the present invention to provide advancements in the art of therapeutic devices.

Another object of the present invention is to provide a therapeutic glove adapted for realizing the benefits of acupressure therapy.

Yet another object of the present invention is to provide a therapeutic glove adapted for realizing the benefits of magnetic therapy.

Still another object of the present invention is to provide a therapeutic glove specifically configured to apply acupressure to the HT-8, PC-8, TH-3, and LI-4 acupoints.

Yet another object of the present invention is to provide a therapeutic glove wherein permanent magnets function as structures for application of acupressure while at the same time providing the benefits of magnetic therapy.

These and other objects are met by the present invention which will become more apparent from the accompanying drawing and the following detailed description of the drawings and preferred embodiments.

DETAILED DESCRIPTION OF THE INVENTION

Figure 1:
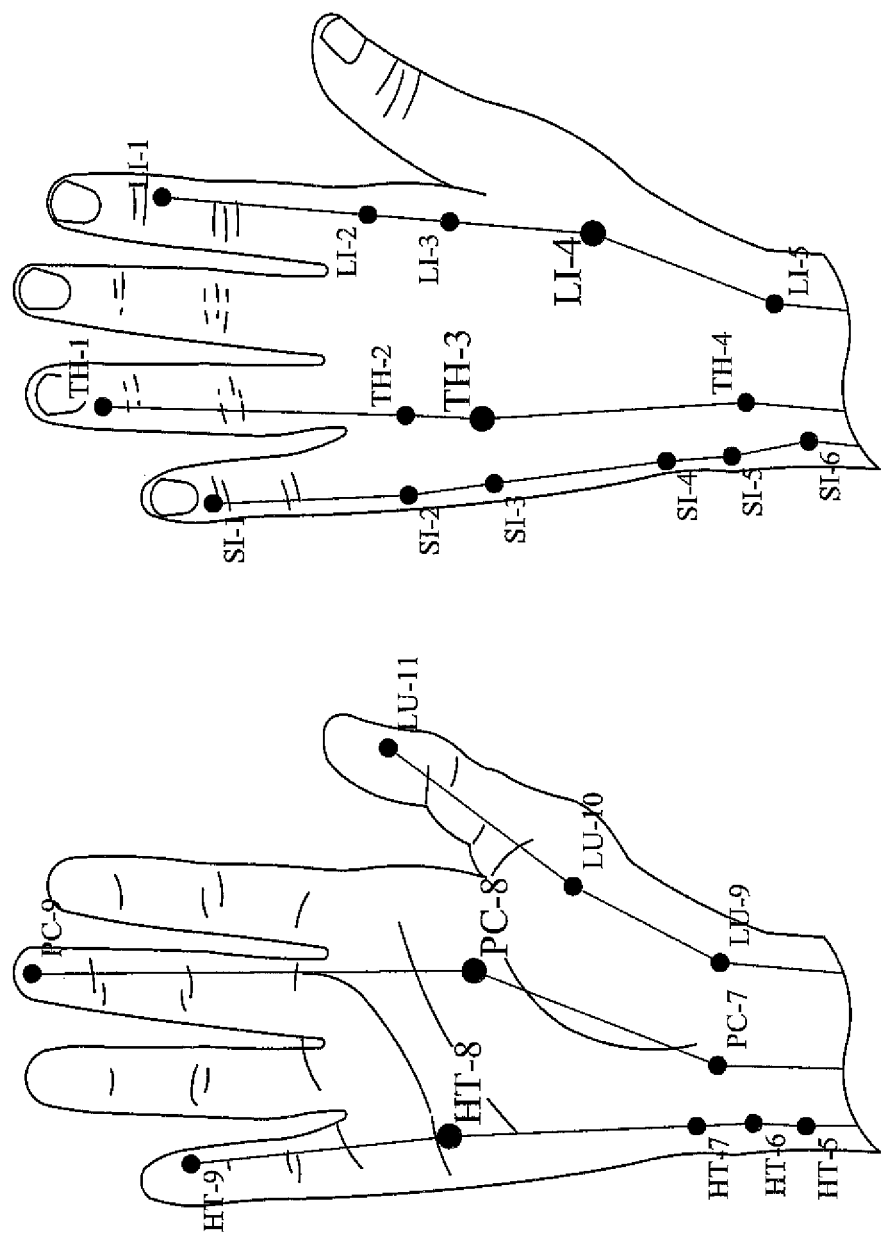
FIG. 1 illustrates recognized acupuncture points connected by corresponding meridian lines on the palm and dorsal sides of the human hand.
Figure 2:
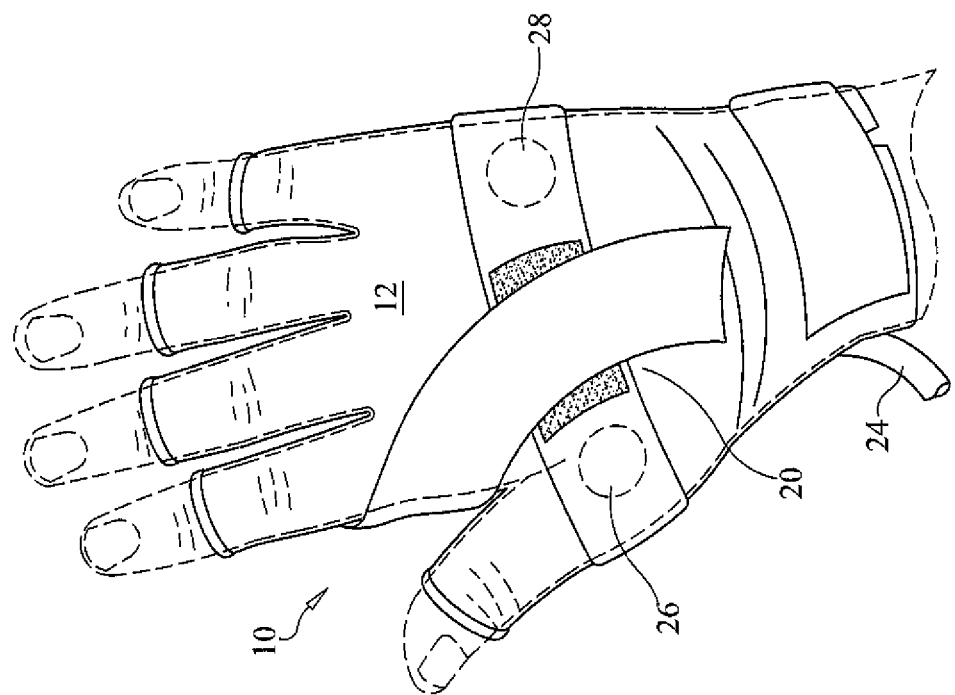
FIG. 2 is a top/dorsal view of a therapeutic glove in accordance with the present invention in operative position on a hand.
Figure 2:
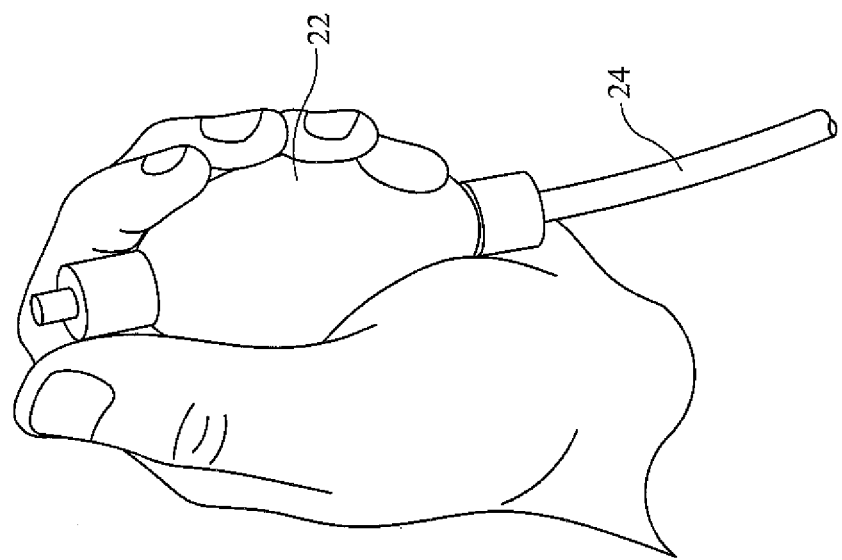
Figure 3:
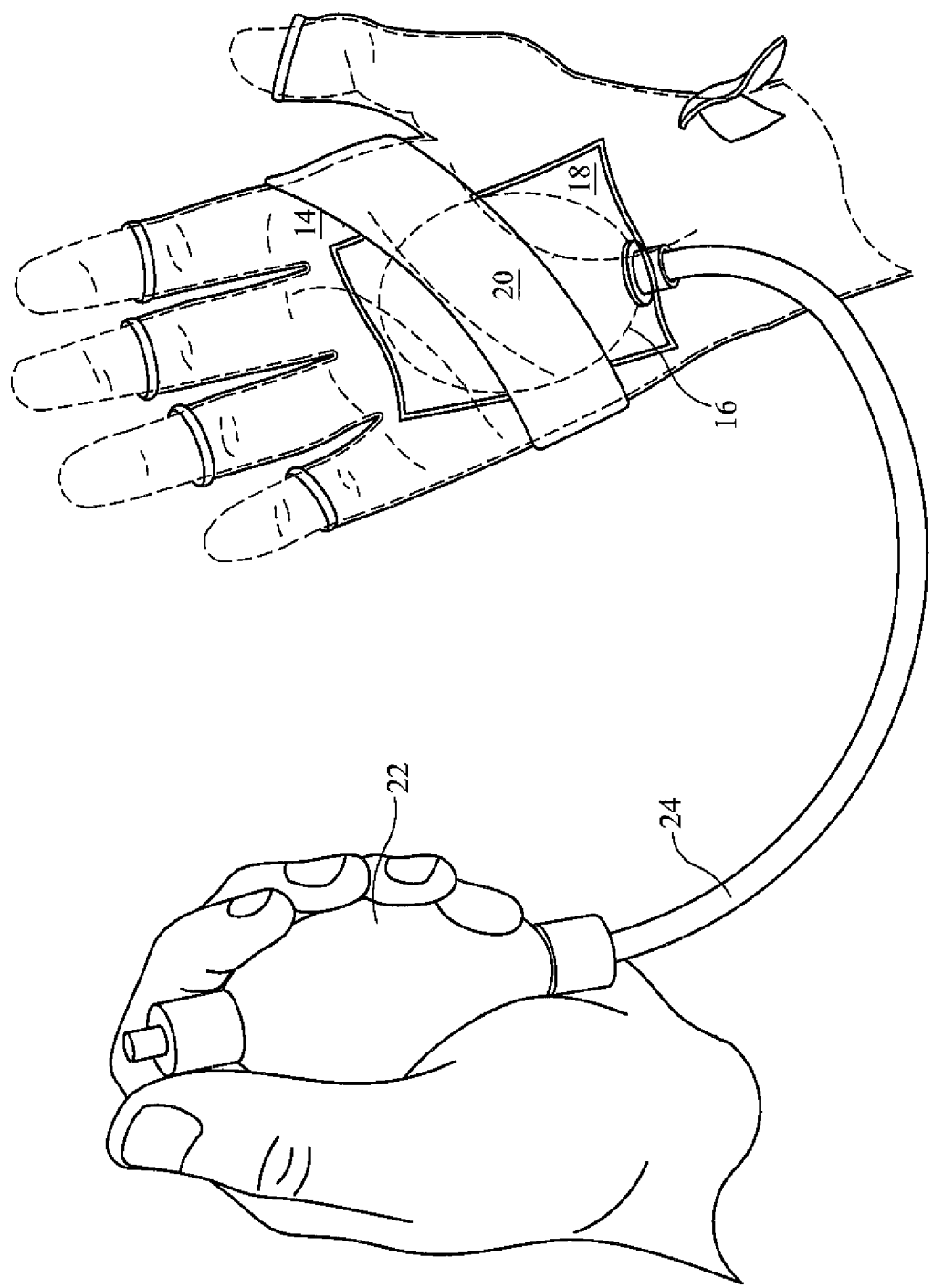
FIG. 3 is a bottom/palm view of a therapeutic glove in accordance with the present invention in operative position on a hand.

With reference now to the drawings, FIG. 1 illustrates acupuncture points connected by corresponding meridian lines on the palm and dorsal sides of the human hand, and FIGS. 2 and 3 depict a therapeutic glove, generally referenced as 10, in accordance with the present invention. More particularly, FIG. 2 depicts a top/dorsal view of a therapeutic glove in accordance with the present invention in operative position on a hand, and FIG. 3 depicts a bottom/palm view of a therapeutic glove in accordance with the present invention in operative position on a hand.

In accordance with the present invention a therapeutic glove 10 is provided and specifically adapted to simultaneously apply a combination of acupressure and magnetic therapy to specific acupoint sites on the hand resulting in unexpected therapeutic benefits, including providing an effective headache remedy. Therapeutic glove 10 preferably comprises a fingerless glove to be worn on the user's hand. As should be apparent, a glove in accordance with the present invention may be provided for each hand, i.e. left-hand and right-hand. FIGS. 2 and 3 illustrate an embodiment for use with the right-hand. Further the term "glove" as used herein shall broadly be construed to include glove-like structures as well as non-glove like structures, such as a configuration of straps capable of attachment to a user's hand while functioning to provide the benefits of acupressure and magnetic therapy as more fully discussed below.

Therapeutic glove 10 includes a dorsal side 12 and palm side 14. Glove 10 is preferably fabricated from a durable yet resilient, stretchable material such as Neoprene, or any other suitable material. A fillable expandable bladder 16 is received within a pocket 18 formed on the palm side 14 of glove 10. Pocket 18 functions to maintain bladder 16 in proper position in the palm region of the glove such that bladder 16 is in covering relation with acupoints HT-8 and PC-8 on the palm of the wearer's hand. Bladder 16 is preferably secured in compression by strap 20, which functions to maintain the bladder in a state of compression as more fully discussed herein. Bladder 16 is connected to a hand-pump 22 by a tube 24 which allows for inflation of bladder 16 by squeezing hand-pump 22. While the preferred embodiment contemplates use of a hand-pump for pressurizing bladder 16, any suitable means for filling the bladder with a fluid (i.e. gas or liquid) is considered within the scope of the present invention. First and second magnets, referenced as 26 and 28, are embedded within the glove 10 and positioned thereon so as to be disposed in covering relation with the LI-4 and TH-3 acupoints points on the side of the wearer's hand. First and second magnets 26 and 28 are preferably disk-shaped permanent ceramic magnets (grade 8) having a surface Gauss of 400. A wrist strap 29 is configured for wrapping around the wearer's wrist and adjustably affixed by mating patches of hook and loop fastening material, referenced as 30a and 30b, to aid in securing the glove to the user's hand.

A significant aspect of the present invention involves providing a therapeutic glove specifically configured to simultaneously apply accupressure to four (4) specific acupoints, namely the HT-8 and PC-8 acupoints on the palm of the hand and the TH-3 and LI-4 acupoints on the dorsal side of the hand. A further significant aspect of the present invention is applying acupressure to the TH-3 and LI-4 acupoints using permanent magnets as pressure application structures whereby the benefits of magnetic therapy are combined with the benefits of acurpressure therapy to maximize therapeutic benefits.

Figure 4:
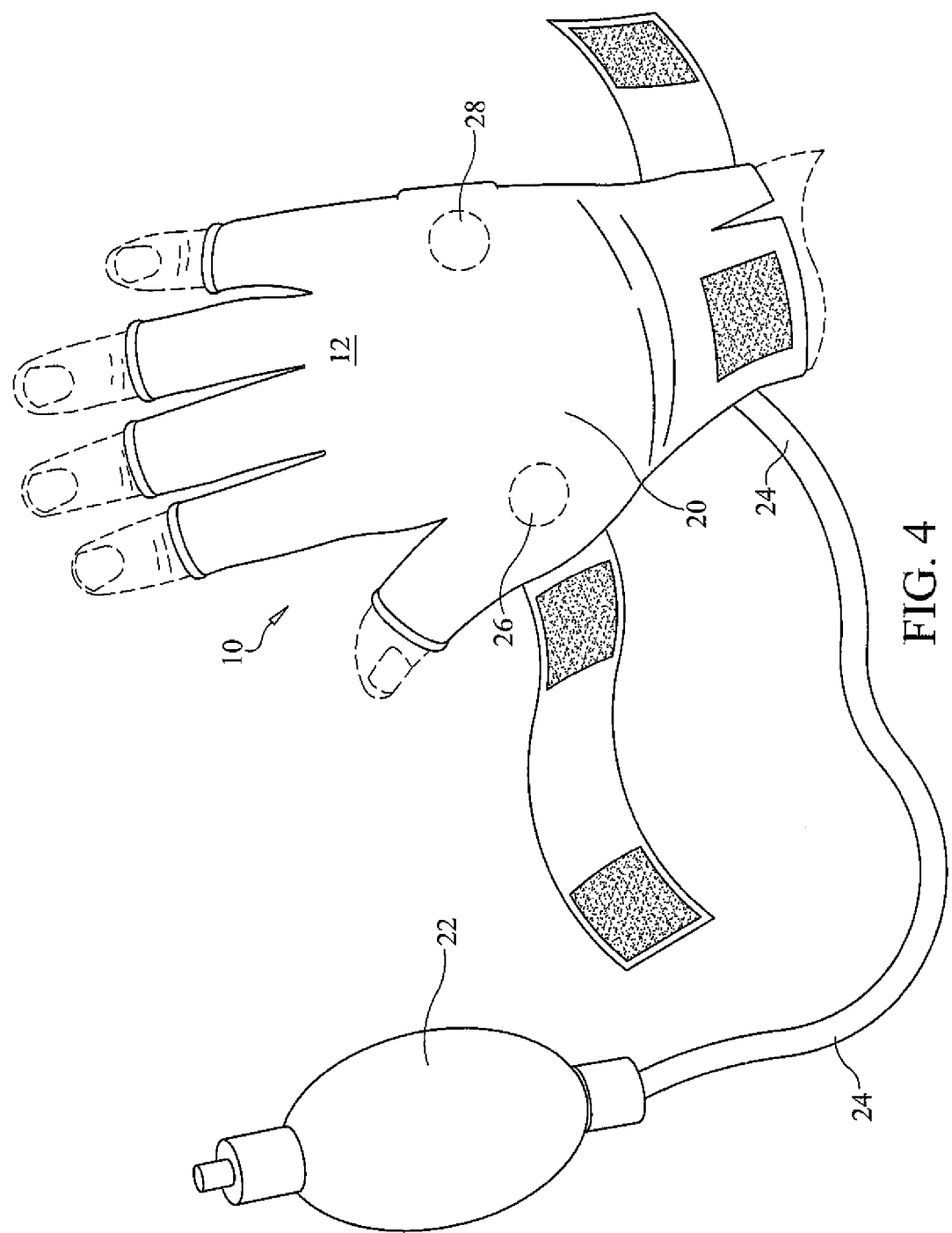
FIG. 4 is a top/dorsal view of a therapeutic glove in accordance with the present invention with straps in an unattached configuration.
Figure 5:
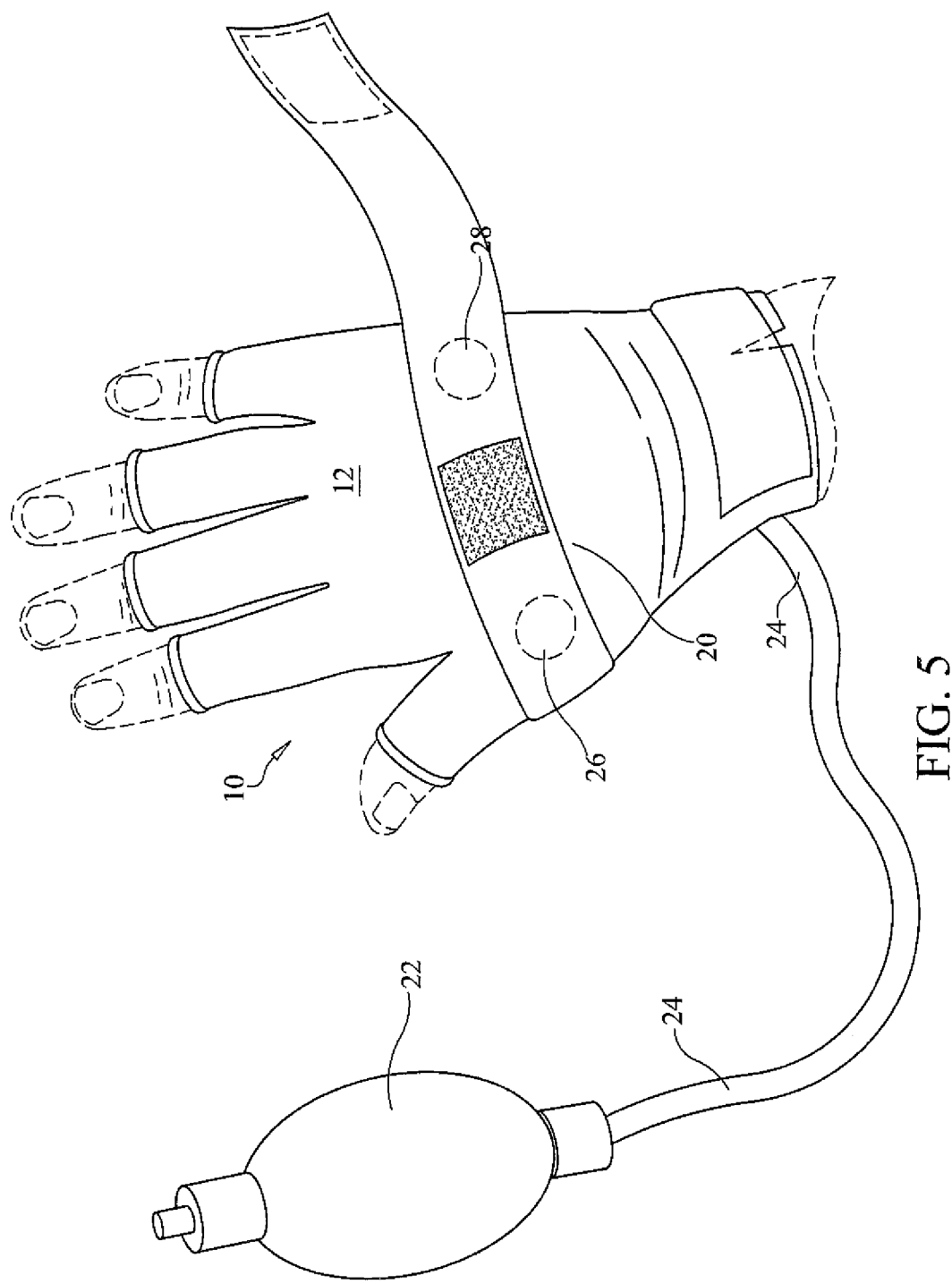
FIG. 5 is a top/dorsal view of a therapeutic glove in accordance with the present invention with the wrist strap operatively attached, and the compression strap wrapped over the dorsal side of the wearer's hand in an unattached configuration.
Figure 6:
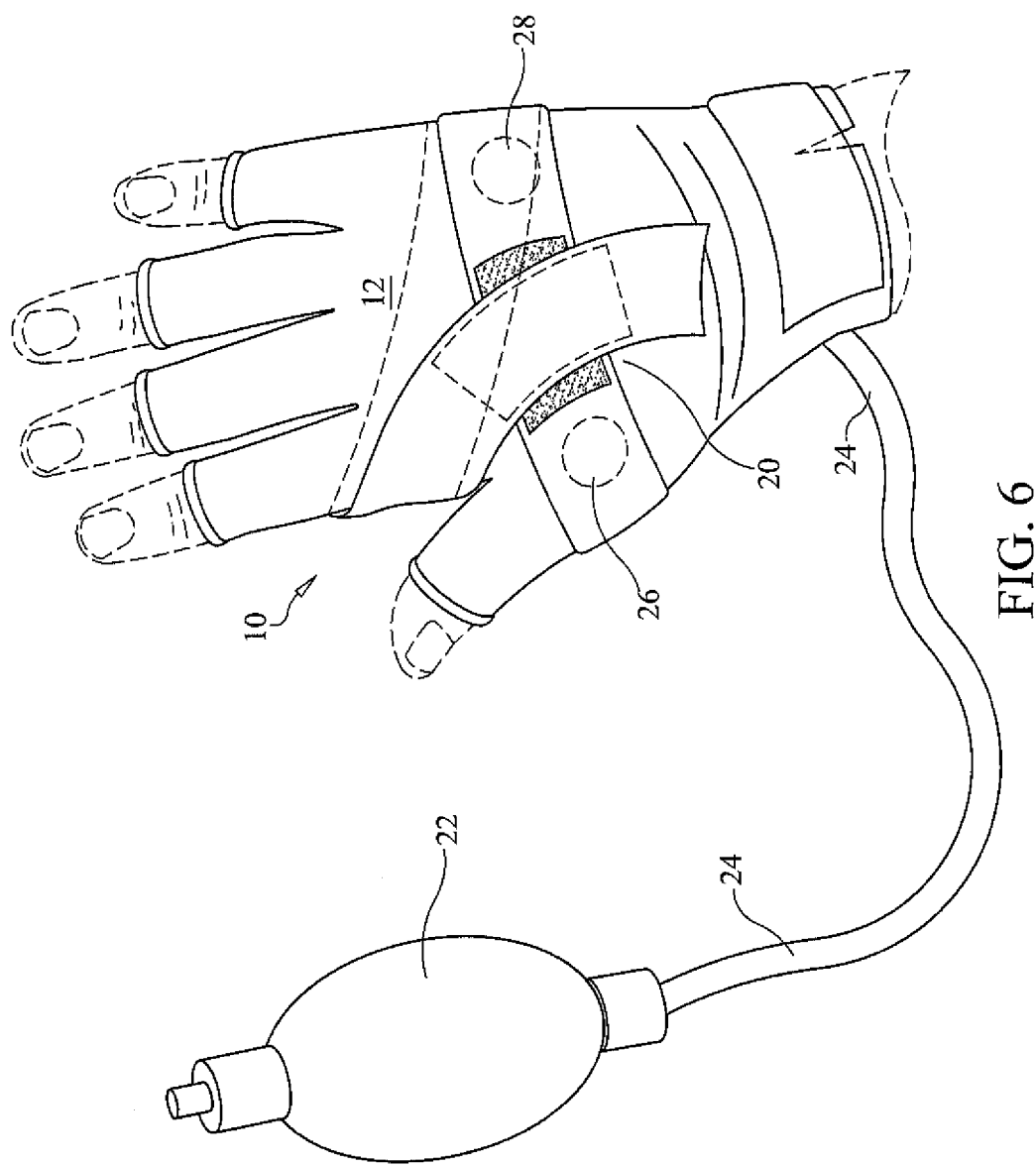
FIG. 6 is a top/dorsal view of a therapeutic glove in accordance with the present invention with the compression strap secured in surrounding relation with the first and second magnets disposed at the LI-4 and TH-3 acupoints, as well as in surrounding relation with the expandable bladder disposed on the palm side of the wearer's hand.

A glove in accordance with the present invention functions to stimulate blood flow to specific areas of the body by applying pressure to four different points on the hand, and has been found to be particularly effective in reliving headaches and other The LI-4 acupoint is located between the index finger and thumb on the dorsal side of the hand. Magnet 26 is attached to the dorsal side 12 of glove 10 so as to be positioned to apply acupressure to the LI-4 acupoint. Accordingly, magnet 26 not only provides rigid structure for application of acupressure, but simultaneously provides magnetic thearapy. The TH-3 acupoint is located between the fourth and fifth metacarpal bones in a depression proximal to the fourth metacarpalphalangeal joint on the dorsal side of the hand. Magnet 28 is attached to the dorsal side 12 of glove 10 so as to be positioned to apply acupressure to the TH-3. Accordingly, magnet 26 not only provides rigid structure for application of acupressure, but simultaneously provides magnetic thearapy. The HT-8 acupoint is located between the fourth and fifth metacarpal bones on the palm side of the hand, and the PC-8 acupoint is located between the second and third metacarpal bones on the palm side of the hand. The fillable pneumatic bladder 16 is attached to the palm side 14 of glove 10 in a location wherein the external surface thereof function to apply pressure to both the HT-8 and PC-8 acupoints. In accordance with a further significant aspect of the preferred embodiment, strap 20 has a first end 20a secured to glove 10 and is intended to wrap around the wearer's hand such that strap to passes directly over magnets 26 and 28 on the dorsal side of the hand, and over bladder 16 on the palm side of the hand, whereafter a patch of hook and loop fastening material 21a disposed on a second opposing end 20b of strap 20 may be secured to a corresponding patch of hook and loop fastening material 21b. Strap 20 thus functions to allow the user to place the glove 10, and particularly magnets 26 and 28, and bladder 16 in compression. Providing a structure to provide such compression maximizes the therapeutic benefits of both acupressure and magnetic therapy by causing magnets 26 and 28 to be pressed onto the corresponding TH-3 and LI-4 acupoints. FIGS. 4-6 depict strap 20 being configured sequentially from an unstrapped to a fully strapped configuration. As should further be apparent, strap 20 may be configured in a number of suitable wrapping configurations so long as at least a portion of strap 20 is disposed in covering relation with magnets 26 and 28 and bladder 16 so as to be capable of providing a compressive force around the wearer's hand.

As should now be apparent, compressive pressure may be adjusted by controlling the amount of air in bladder 16, and hence the amount of expansion thereof, using the attached hand pump 22, as well as by adjustment of strap 20. As the pressure level within the bladder increased, the bladder will expand thereby applying increased pressure to the specified acupoints on the user's hand. The amount of pressure required is individualized, depending upon the severity of the headache, or pain. The greater the pressure applied, the greater the energy flow throughout the body. The treatment is intended to work within ten to twenty minutes, and may be used several times a day, or as needed. The glove is comfortable and transportable, and utilizes magnets on the indicated pressure points and air pressure from the bladder to achieve beneficial results by combining the therapeutic effects of acupressure and magnetic therapy.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A therapeutic apparatus for administering acupressure and magnetic therapy to acupoints on a wearer's hand including the LI-4, TH-3, HT-8 and PC-8 acupoints, said apparatus comprising:

a glove to be worn on the hand, said glove having a dorsal side and a palm side;

first and second permanent magnets attached to the dorsal side of said glove, said first magnet disposed to apply acupressure to the wearer's LI-4 acupoint, said second magnet disposed to apply pressure to the wearer's TH-3 acupoint;

an expandable bladder attached to the palm side of said glove and disposed to apply pressure to the wearer's HT-8 and PC-8 acupoints;

a pump pneumatically connected to said bladder to allow for the selective pressurization and depressurization of said bladder; and a strap configured to wrap around the wearer's hand such that the strap passes over said first and second permanent magnets on the dorsal side of said glove and over said expandable bladder on the palm side of said glove.

2. A therapeutic apparatus according to claim 1, wherein said strap functions to place said first and second magnets and said expandable bladder in compression so as to bias said magnets towards the LI-4 and TH-3 acupoints from the dorsal side of the glove.

3. A therapeutic apparatus according to claim 1, wherein said strap is removably secured in compressive relation with said glove by hook and loop fastening material.

4. A method of administering acupressure and magnetic therapy to acupoints on a wearer's hand including the LI-4, TH-3, HT-8 and PC-8 acupoints, said method comprising:

providing a glove to be worn on the wearer's hand, said glove having a dorsal side and a palm side;

said glove including first and second permanent magnets attached to the dorsal side thereof, said first magnet disposed to apply acupressure to the wearer's LI-4 acupoint, said second magnet disposed to apply pressure to the wearer's TH-3 acupoint;

said glove including an expandable bladder attached to the palm side of said glove and disposed to apply pressure to the wearer's HT-8 and PC-8 acupoints;

providing a pump pneumatically connected to said bladder to allow for the selective pressurization and depressurization of said bladder;

providing a strap configured to wrap around the wearer's hand such that the strap passes over said first and second permanent magnets on the dorsal side of said glove and over said expandable bladder on the palm side of said glove;

fitting said glove to the wearer's hand and configuring said strap around the wearer's hand such the strap passes over said first and second permanent magnets on the dorsal side of said glove and over said expandable bladder on the palm side of said glove;

actuating said pump to pressurize said bladder to a desired pressurization.

* * * * *